(12) United States Patent
Pattee

(10) Patent No.: US 6,615,428 B1
(45) Date of Patent: Sep. 9, 2003

(54) DUAL STAGE TELESCOPING IMAGING TABLE

(75) Inventor: Jeffrey Wayne Pattee, Salt Lake City, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/688,522

(22) Filed: Oct. 16, 2000

(51) Int. Cl.[7] .................. A61G 13/00; A61G 13/02; A61G 13/12
(52) U.S. Cl. ............... 5/601; 5/943; 108/143; 378/209
(58) Field of Search ................ 5/601, 943, 600; 108/143; 378/209

(56) References Cited

U.S. PATENT DOCUMENTS

| | | | |
|---|---|---|---|
| 4,475,072 A | 10/1984 | Schwehr et al. | 318/602 |
| 4,541,293 A | 9/1985 | Caugant et al. | 74/89.18 |
| 4,657,235 A | 4/1987 | Schar | 269/322 |
| 5,199,060 A | 3/1993 | Kato | 378/196 |
| 5,272,776 A * | 12/1993 | Kitamura | 5/943 |
| 6,240,582 B1 * | 6/2001 | Reinke | 5/661 |

\* cited by examiner

Primary Examiner—Alexander Grosz
(74) Attorney, Agent, or Firm—McAndrews, Held & Malloy, Ltd.; Peter J. Vogel; Michael A. Dellapenna

(57) ABSTRACT

A system and method for positioning a medical imaging table in an imaging apparatus is presented. The imaging table includes a fixed plate, a second stage, a first stage and a gearing system. The first stage includes an imaging tabletop. The gearing system includes a pinion gear and gear racks mounted on the first and second stages. The stages of the system are geared together to move simultaneously. The imaging table is able to extend and or retract smoothly because the stages are geared together. Further, because the imaging table extends through a first stage, a second stage, and a fixed plate, the tabletop of the imaging table is more compact with a larger imaging area.

16 Claims, 7 Drawing Sheets

DUAL STAGE TELESCOPING IMAGING TABLE

FIELD OF THE INVENTION

The present invention generally relates to an imaging table for use in medical imaging systems. More particularly, the present invention relates to a dual stage imaging table wherein the stages are geared together to move simultaneously.

BACKGROUND OF THE INVENTION

Medical imaging systems, such as X-ray imaging systems, typically include an emitter, a detector, and an imaging table. In operation, the imaging table, on which patients are positioned, is positioned between the emitter and the detector. The emitter typically emits radiation, such as X-rays, toward the patient. The radiation typically passes through the patient positioned on the imaging table and encounters the detector. As the radiation passes through the patient, anatomical structures inside the patient cause spatial variances in the radiation received at the detector. The detector then translates the radiation variances into an image which may be employed for clinical evaluations.

As mentioned above, while imaging, the patient is positioned on an imaging table. The imaging table supports the patient but is mostly transparent to the imaging radiation so as to not interfere with the imaging of the patient. Proper positioning of the patient on the imaging table is important for a variety of reasons. For example, some imaging devices operate in confined areas. Further, positioning a patient within the imaging chamber of an imaging device may be awkward and difficult.

In order to assist in the proper positioning of the patient in the imaging device, some imaging tables include an additional portion, or stage, that extends and retracts. In operation, a patient is positioned on the stage and the stage is extended to optimize the patient's position within the imaging device. Typically, imaging tables extend and retract through one stage. The stage extends from the base of the imaging device. Commercially available imaging tables typically include a fixed plate and a movable stage. The movable stage is grasped and pulled to extend, or pushed to retract.

The use of bearing rails are employed to facilitate movement of the stage. Typically, the stage slides over the rails, or the rails slide over supprts, to extend or retract. Full extension or retraction of the imaging table depends on the full extension or full retraction of the stage. Because the stage may extend, the stage typically requires support.

The stage is typically supported by bearing rails. Typically, the bearing rails are as long as the length of extension. The total amount the stage extends is known as the length of extension. Therefore, as a stage is extended, the bearing rails that support the stage are extended. The bearing rails may protrude into the work area of the imaging device.

Typically an abrupt transition between the fixed plate and the extending stage may cause discomfort to the patient positioned on the imaging table. For example, an abrupt transition may aggravate the patient's medical condition, or cause a patient to become nervous, agitated, or anxious with regard to the imaging procedure.

Thus, a need has long existed for a an improved imaging table with improved range of extension and retraction. Additionally, a need has existed for an imaging table with a larger imaging area. A need has also existed for a more compact imaging table. Additionally, a need has existed for an imaging table with smooth positioning.

SUMMARY OF THE INVENTION

The present invention includes an imaging table for use in an imaging apparatus. The imaging table includes a fixed plate, a second stage, a first stage, and a gear system. The first stage includes an imaging tabletop for positioning a patient to be imaged. The gear system includes a pinion gear mounted in the second stage as well as gear racks mounted on the fixed plate and first stage that operatively engage the pinion gear.

The gear system enables the first stage of the imaging table to smoothly extend from, and retract to, the fixed plate. The first stage and second stage are geared together to move simultaneously.

These and other features of the present invention are discussed or apparent in the following detailed description of the preferred embodiments of the present invention.

DETAILED DESCRIPTION OF THE PREFERRED EMBODIMENT

Figure 1:
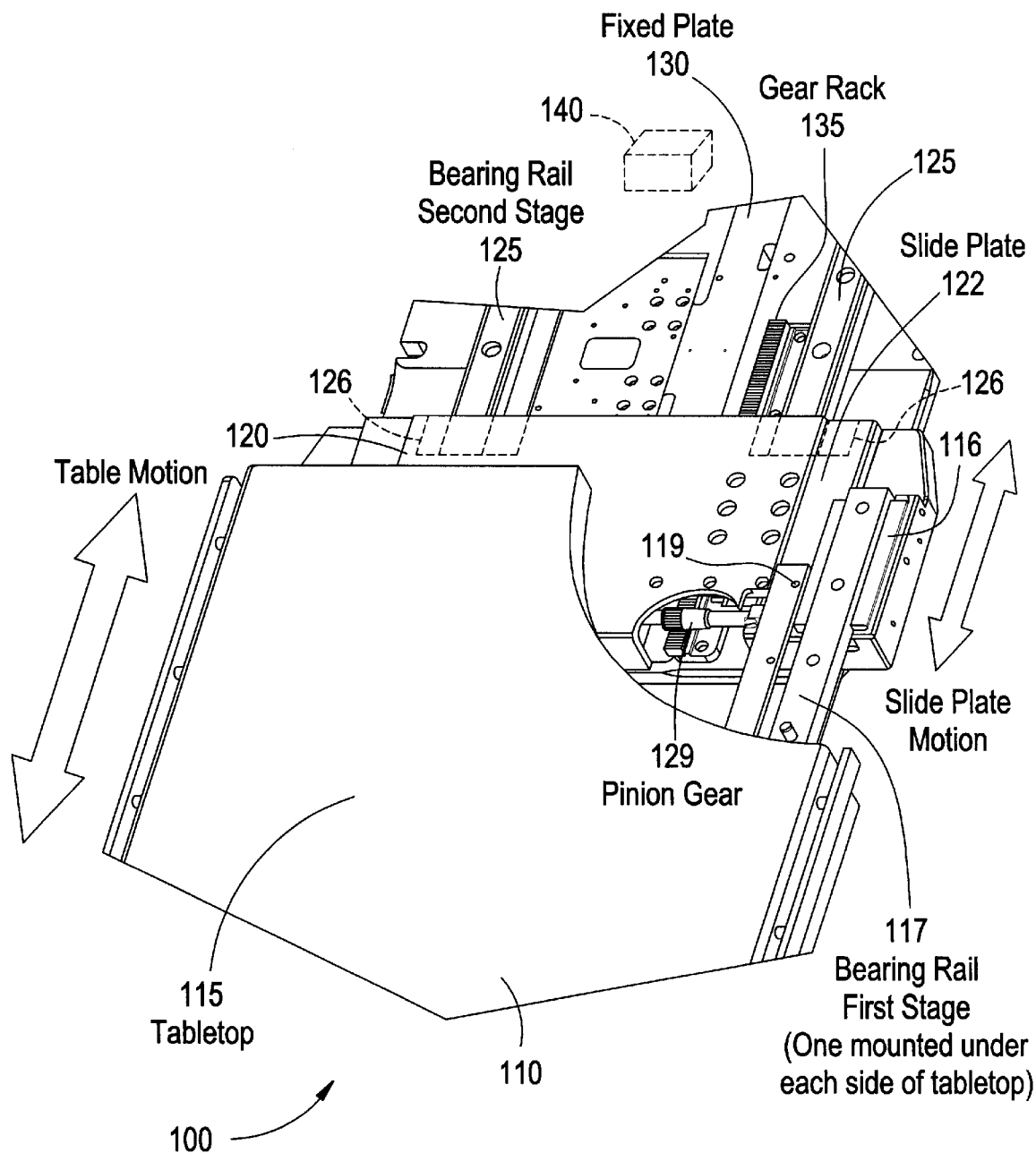
FIG. 1 illustrates a dual stage telescoping imaging table according to a preferred embodiment of the present invention.

FIG. 1 illustrates a dual stage telescoping imaging table 100 according to a preferred embodiment of the present invention. The imaging table 100 includes a first stage 110, a second stage 120, and a fixed plate 130. The first stage 110 includes a table top 115, first stage bearing rails 117, and a first stage gear rack 119. The second stage 120 includes a slide plate 122, first stage supports 116, second stage supports 126, and a pinion gear 129. The fixed plate 130 includes stop blocks 140, second stage bearing rails 125, and a second stage gear rack 135.

The fixed plate 130 supports the second stage 120 which in turn supports the first stage 110. That is, the fixed plate 130 includes second stage bearing rails 125 that support the second stage supports 126. The second stage supports 126 support the second stage 120. The second stage 120 includes first stage supports 116 that support the first stage bearing rails 117. The first stage bearing rails 117 are connected to the first stage 110. The first stage supports 116 and the second stage supports 126 slide on the first stage bearing rails 117 and the second stage bearing rails 125, respectively.

Figure 2:
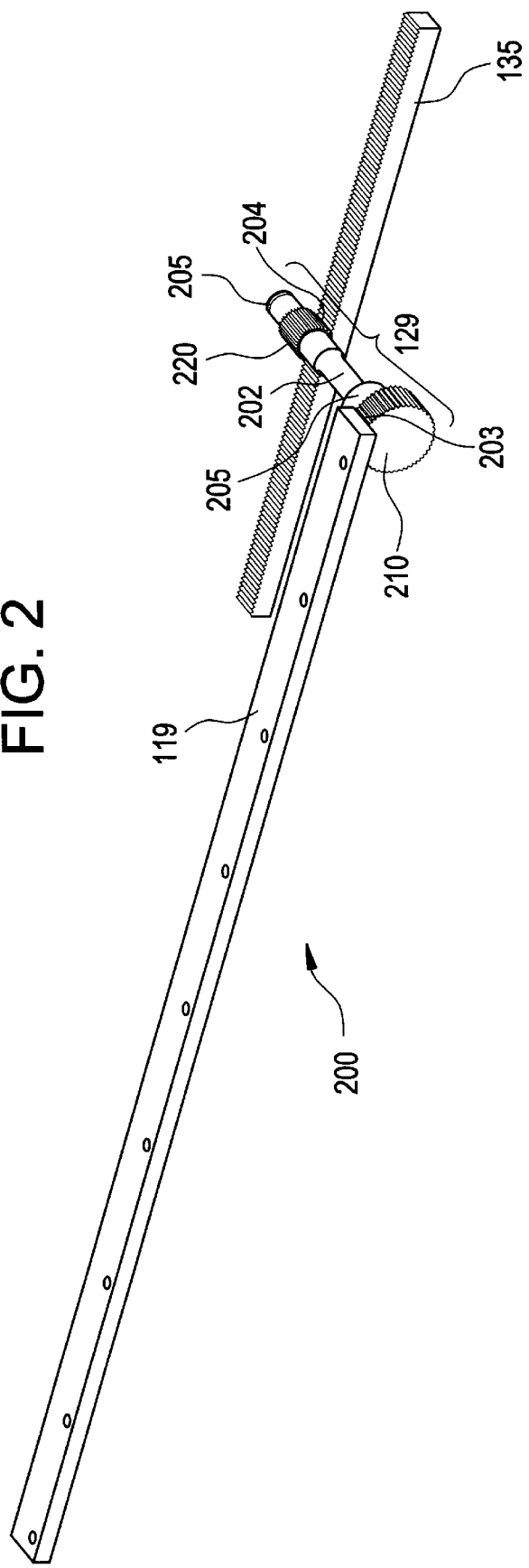
FIG. 2 illustrates a gear system according to a preferred embodiment of the present invention.

FIG. 2 illustrates a gear system 200 included within the second stage 120 of the imaging table 100. FIG. 2 illustrates a gear system 200 according to a preferred embodiment of the present invention. The gear system 200 includes a pinion gear 129, a first stage gear rack 119, a first gear contact 203, a second stage gear rack 135, a second gear contact 204 and extensors 205. The pinion gear 129 includes an axle 202, a first engaging gear 210, and a second engaging gear 220.

The pinion gear 129 may be fixed within the second stage 120 by the extensors 205. The extensors 205 extend into a fixed structure within the second stage 120 to hold the pinion gear 129 in the second stage 120. The first engaging gear 210 and the second engaging gear 220 are connected to the axle 202 at opposite ends. The first engaging gear 210 contacts the first stage gear rack 119 at the first gear contact 203. The second engaging gear 220 contacts the second stage gear rack 135 at the second gear contact 204.

Figure 3:
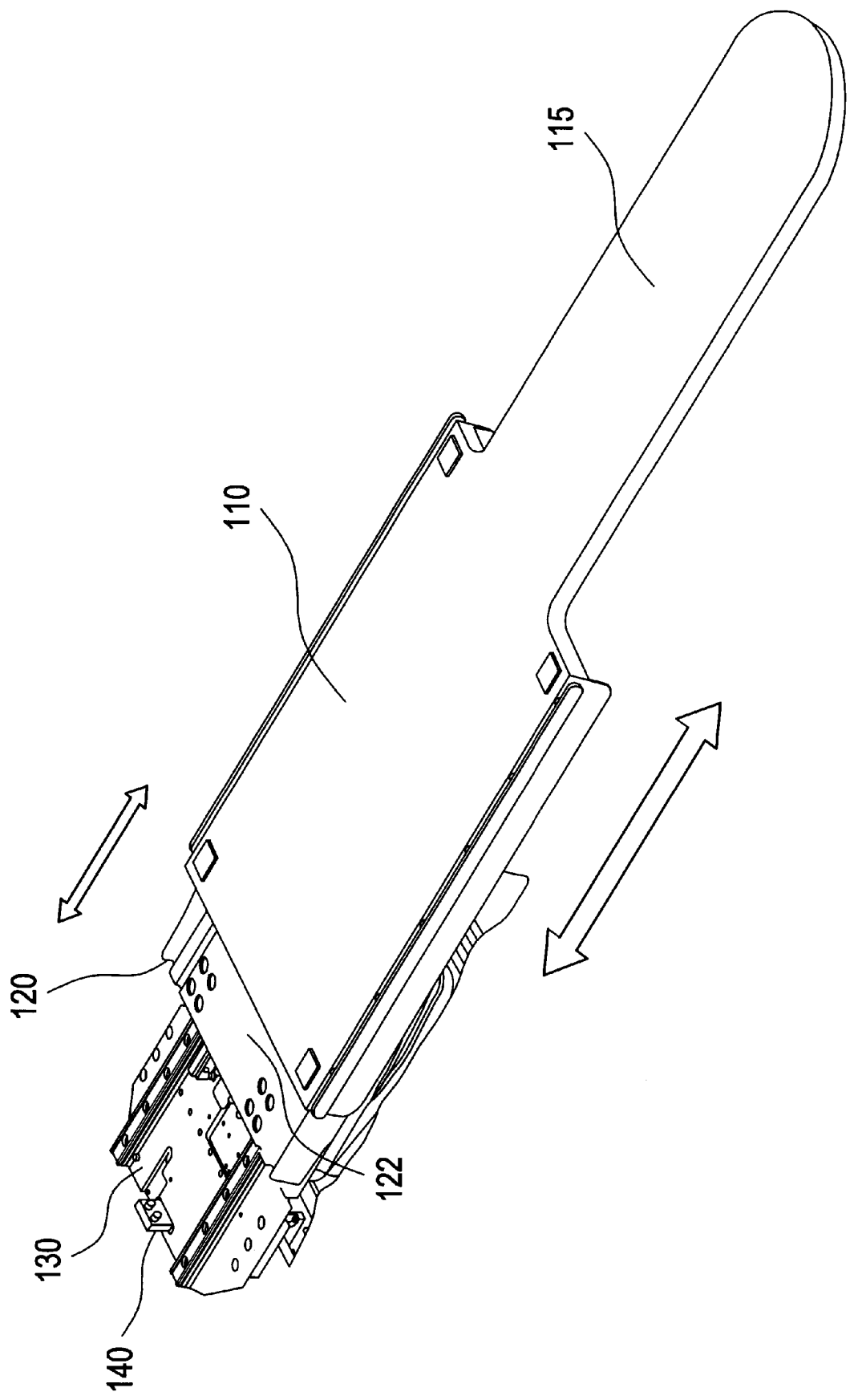
FIG. 3 illustrates a perspective top view of the dual stage telescoping imaging table of FIG. 1 according to a preferred embodiment of the present invention.
Figure 4:
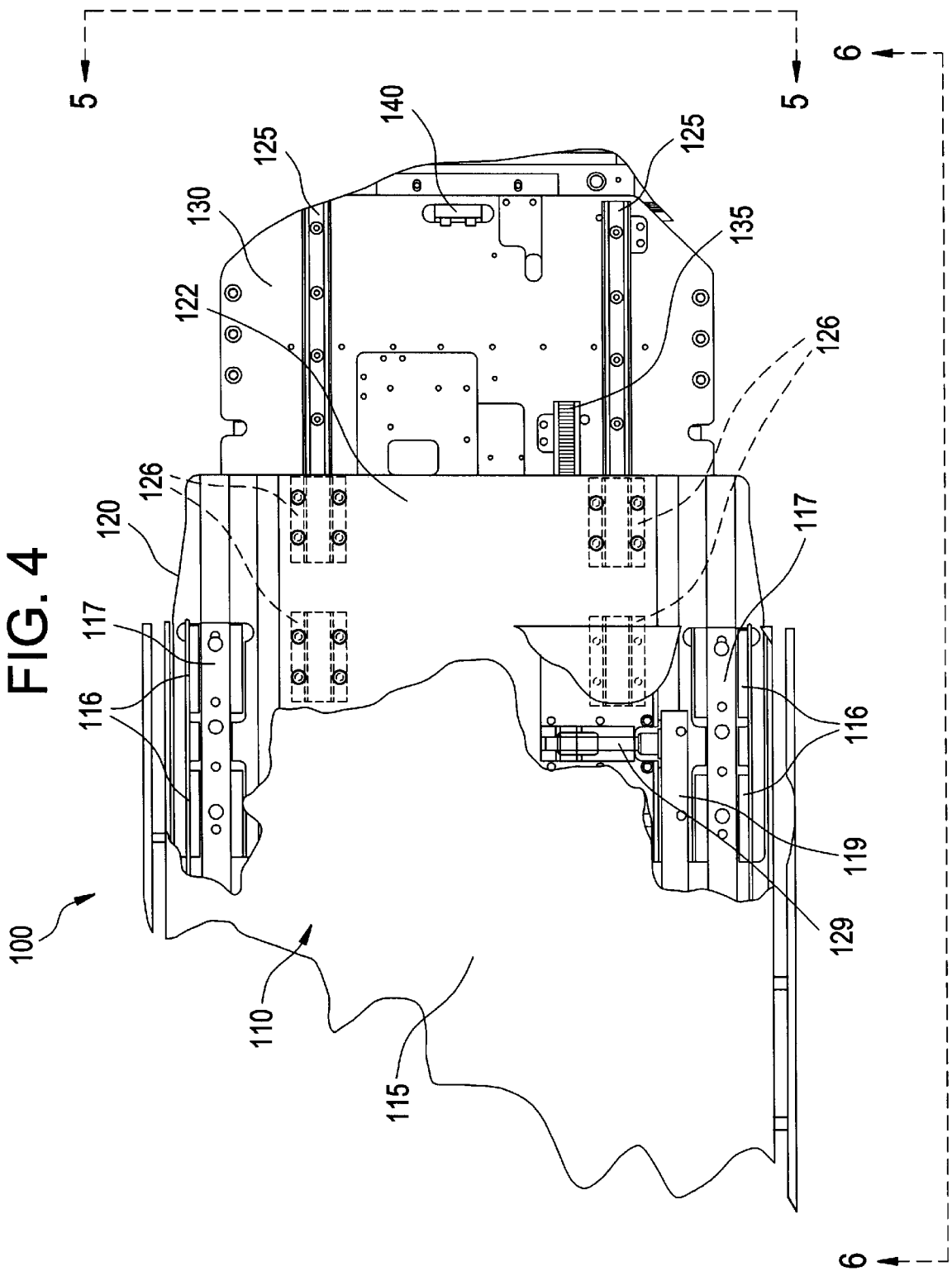
FIG. 4 illustrates a partial top sectional view of the dual stage telescoping imaging table of FIG. 1 according to a preferred embodiment of the present invention.
Figure 5:
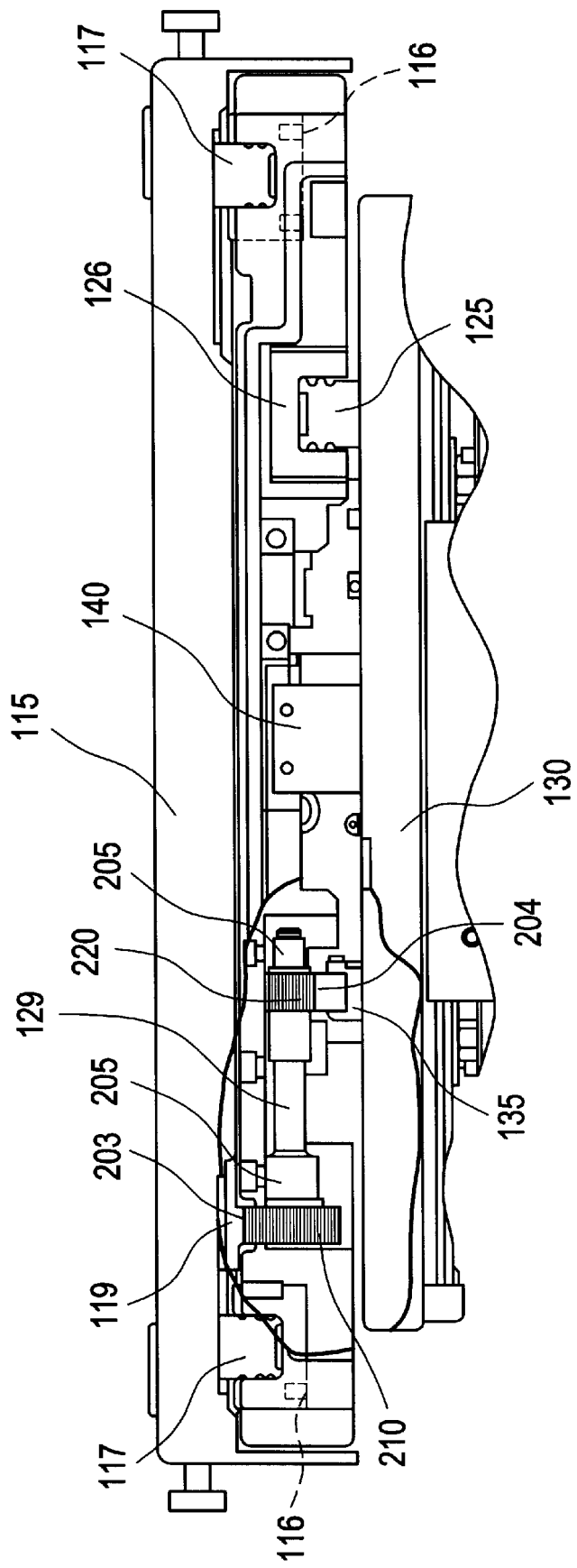
FIG. 5 illustrates an end view of the dual stage telescoping imaging table of FIG. 1 according to a preferred embodiment of the present invention.
Figure 6:
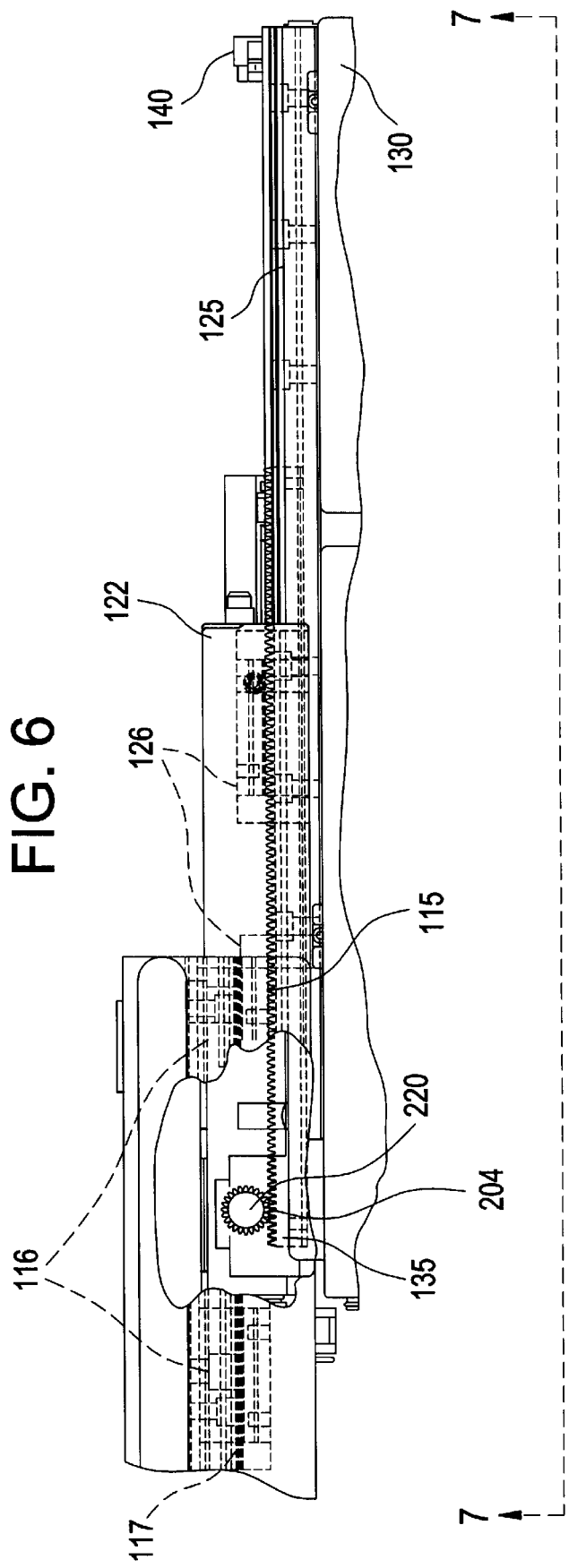
FIG. 6 illustrates a side transparency view of the dual stage telescoping imaging table of FIG. 1 according to a preferred embodiment of the present invention.
Figure 7:
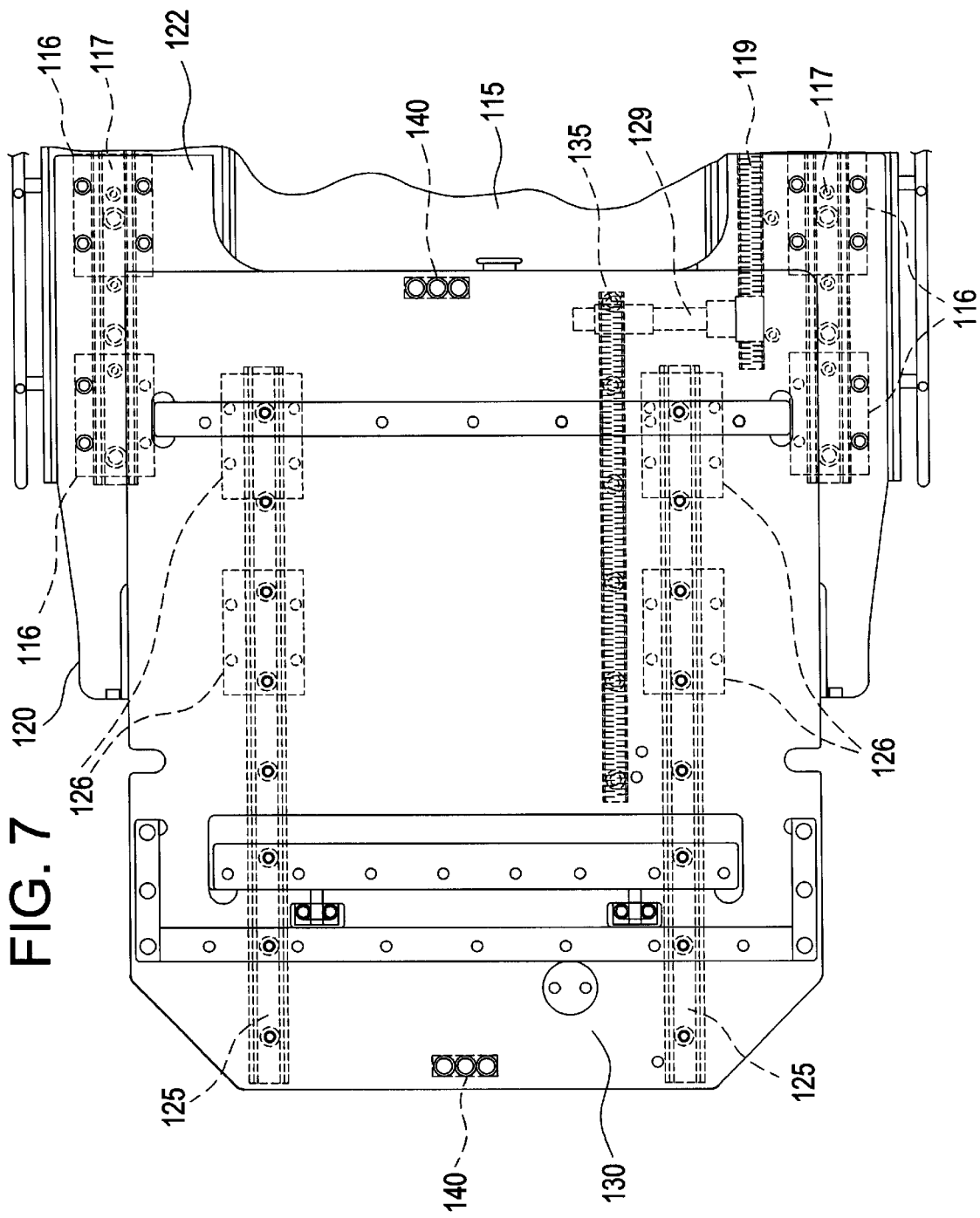
FIG. 7 illustrates a partial bottom transparency view of the dual stage telescoping imaging table of FIG. 1 according to a preferred embodiment of the present invention.

FIG. 3 illustrates a perspective top view of the dual stage telescoping imaging table of FIG. 1 according to a preferred embodiment of the present invention. The imaging table 100 includes a first stage 110, a tabletop 115, a second stage 120, a slide plate 122, a fixed plate 130, and a stop block 140. The directions of motion of the first stage 110 relative to the fixed plate 130 are indicated by arrows.

FIGS. 4, 5, 6 and 7 illustrate various views of the dual stage telescoping imaging table of FIG. 1 according to a preferred embodiment of the present invention. The imaging table 100 includes a first stage 110, a second stage 120, and a fixed plate 130. The first stage 110 includes a table top 115, first stage bearing rails 117, and a first stage gear rack 119. The second stage 120 includes a slide plate 122, first stage supports 116, second stage supports 126, and a pinion gear 129. The fixed plate 130 includes stop blocks 140, second stage bearing rails 125, and a second stage gear rack 135.

The second stage bearing rails 125 are connected to fixed plate 130 and support the second stage supports 126. The second stage supports 126 are connected to slide plate 122. The first stage supports 116 are connected to slide plate 122. The first stage bearing rails 117 are connected to the table top 115 and are supported by the first stage supports 116. The first stage supports 116 and the second stage supports 126 slide on the first stage bearing rails 117 and the second stage bearing rails 125, respectively.

As shown in FIGS. 4, 5, 6 and 7, the pinion gear 129 of the gear system 200 illustrated in FIG. 2 is fixed within the second stage 120. The extensors 205 extend into a fixed structure within the second stage 120 to hold the pinion gear 129 in the second stage. The first engaging gear 210 contacts the first stage gear rack 119 at the first gear contact 203. The second engaging gear 220 contacts the second stage gear rack 135 at the second gear contact 204.

In operation, movement of the first stage 110 causes the first stage gear rack 119 to move because the first stage gear rack 119 is connected to the first stage 110. As the first stage gear rack 119 moves, the first stage gear rack 119 causes the first engaging gear 210 to rotate because the first stage gear rack 119 and the first engaging gear 210 are operatively engaged. The rotation of the first engaging gear 210 causes the axle 202 to rotate because the first engaging gear 210 is connected to the axle 202. The rotation of the axle 202 causes the second engaging gear 220 to rotate. The second engaging gear 220 operatively engages the second stage gear rack 135. When the second engaging gear 220 rotates, the pinion gear 129 and extensors 205 move on the second stage gear rack 135 in response to the rotation of the second engaging gear 220. Because the second stage gear rack 135 is connected to the fixed plate 130, the second stage 120 moves relative to the fixed plate 130. Thus, the first stage 110 moves relative to the second stage 120, and the second stage 120 moves relative to the fixed plate 130 resulting in an overall movement of the first stage 10 relative to the fixed plate 130.

Preferably, the diameter of the first engaging gear 210 is twice the diameter of the second engaging gear 220. Because the diameter of the first engaging gear 210 is twice the diameter of the second engaging gear 220, the first stage gear rack 119 moves twice as fast as the second stage gear rack 135. Additionally, the first stage gear rack 119 moves twice the distance the second stage gear rack 135 moves. Consequently, the first stage 110 moves twice as fast as, and twice the distance, of the second stage 120. The movement of the first stage 110 and the second stage 120 is further described below.

Alternatively, the diameter of the first engaging gear 210 may be the same as that of the second engaging gear 220. Also, alternatively, the diameter of the engaging gears 210 and 220 may be in different proportions.

Referring again to FIG. 1, in operation, a patient to be imaged may be positioned on the tabletop 115 of the first stage 110. Then, the first stage 110 may be extended to position the patient for imaging. After the first stage 110 has been fully extended, the imaging device (not shown) may be used to image portions of the patient's body. Once the imaging is complete, the first stage 110 may be retracted, and the patient removed.

The first stage 110 may be extended by an operator grasping and pulling the first stage 110. As the first stage 110 is grasped and pulled, the second stage 120 moves in response to the grasping and pulling of the first stage 110 because the second stage 120 is operatively connected to the first stage by the gear system as described above with reference to FIG. 2. That is, the first stage 110 includes the first stage gear rack 119, and the second stage 120 includes the pinion gear 129 and as described above. Consequently, movement of the first stage 110 engages the pinion gear 129 of the second stage 120 to move thereby causing movement in the second stage 120. That is, as the first stage 110 is grasped and pulled, the first stage gear rack 119 causes rotation of the pinion gear 129 of the second stage 120 because the first stage gear rack 119 and the pinion gear 129 are operatively engaged. As the pinion gear 129 rotates, it traverses the second stage gear rack 135 because the pinion gear 129 and the second stage gear rack 135 are operatively engaged. Thus, as the first stage 110 is grasped and pulled, the motion of the first stage 110 causes the pinion gear 129 to move which in turn moves the second stage 120.

Once the first stage 110 reaches its fullest extent, the motion of the first stage 110 may be arrested by the stop block 140. Preferably the fixed plate includes two stop blocks 140. One stop block 140 is located at the front and center of the fixed plate 130, while the other stop block 140 is located at the rear and center of the fixed plate 130. In operation, when the first stage 110 reaches its full extent, a portion of the second stage 120 contacts the front stop block 140 and arrests the motion of the second stage 120. Because the first stage 110 and the second stage 120 are geared together, stopping the second stage 120 arrests the motion of the first stage 110. Consequently, the front stop block 140 stops the first stage 110 and the second stage 120 from further extending.

To retract the imaging table 100, the first stage 110 may be grasped by an operator and pushed toward the fixed plate 130. As the first stage 110 is grasped and pushed, the second stage 120 moves in response to the grasping and pushing of the first stage 110 because the second stage 120 is operatively connected to the first stage 110 by the gear system 200. That is, as the first stage 110 is grasped and pushed, the first stage gear rack 119 causes the pinion gear 129 of the second stage to rotate because the first stage gear rack 119 and the pinion gear 129 are operatively engaged. The pinion gear 129 causes traverses the second stage gear rack 135 because the pinion gear 129 and the second stage gear rack 135 are operatively engaged. As the first stage 110 is grasped and pushed, the motion of the first stage 110 causes motion of the pinion gear 129 which in turn moves the second stage 120. When the first stage 110 reaches the point of full retraction, a portion of the second stage 120 contacts the rear stop block 140 and arrests the motion of the second stage 120. Because the first stage 110 and the second stage 120 are geared together, stopping the second stage 120 arrests the motion of the first stage 110. Consequently, the rear stop block 140 stops the first stage 110 and the second stage 120 from further retracting.

The preferred embodiment of the present invention provides a tabletop 115 having a greater imaging area included within a more compact imaging table 100 as compared to the prior art. The imaging area of the preferred embodiment is greater, and the imaging table 100 is more compact, because the first stage bearing rails 117 and the second stage bearing rails 125 are telescopic. For example, the imaging and work area of the tabletop 115 of the preferred embodiment is greater because the first stage bearing rails 117 do not protrude into the tabletop 115 to the same extent as do the bearing rails of the prior art.

The prior art tabletop includes a single moving stage and is supported by bearing rails attached to the fixed or moving stage. In the prior art, the bearing rails must be long enough to support the movable stage yet remain fixed to the fixed stage. The preferred embodiment, however extends through a fixed plate 130, a second stage 120 and a first stage 110. The first stage bearing rails 117 and the second stage bearing rails 125 overlap each other. The second stage 120 does not protrude into the imaging area. Only the tabletop 115 of the first stage may protrude into the imaging area. Because the first stage 110 and the second stage 120 are mounted on the first stage bearing rails 117 and the second stage bearing rails 125 respectively, the first stage 110 and the second stage 120 may telescope outward to provide for greater extension and more compact storage than the prior art.

Additionally, the imaging table 100 does not abruptly transition. That is, the imaging table 100 extends and retracts smoothly from its initial to final positions without physically jarring, abrupt transitions. The imaging table 100 extends and retracts smoothly because the first stage 110 and the second stage 120 are geared together to move simultaneously.

Additionally, the imaging table 100 requires at least one stop block 140 on the fixed plate 130 to stop both the first stage 110 and the second stage 120. Only stop blocks 140 on the fixed plate may be required because arresting the motion of any one stage arrests the motion of the other stage because the stages 110 and 120 are geared together. The gear system 200 allows the first stage 110 and second stage 120 to extend and retract smoothly without stopping during extension or retraction. Extension is smooth and continuous because the first stage 110 and the second stage 120 are geared together. Alternatively, the stop blocks 140 may be positioned on the second stage 120 or the first stage 110.

As an alternative to manually positioning the imaging table 100, the imaging table 100 may be equipped for automatic positioning. That is, instead of the operator pushing or pulling to retract or extend the imaging table 100, the imaging table 100 may be connected to a motorized control system (not shown). The motorized control system may be employed to extend or retract the imaging table. For example, the motorized control system may engage the pinion gear 129 to extend or retract the imaging table 100. The motorized control system preferably includes a user interface to allow operator control of the imaging table 100.

Alternatively, the preferred embodiment of the present invention may not be limited to two stages. Instead, more stages may be employed. For example, three stages may be employed. In such a system, the fixed plate may support the third stage. The third stage may support the second stage which may support the first stage. The alternative imaging device having three stages may require an additional gear system. That is, an additional pinion gear and gear rack may be placed between the fixed plate and the third stage.

Also, as an alternative to the stop block 140, the imaging device 100 may be stopped in a variety of ways. For example, more than one stop block 140 may be employed. Alternatively, grooves or risers in the gear racks may be formed that halt the progress of the motion of the gears.

While particular embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features which come within the spirit and scope of the invention.

What is claimed is:

1. A system for positioning an imaging table in an imaging apparatus, said system including:
   a first stage;
   a second stage;
   a fixed plate; and
   a pinion gear mounted in said second stage wherein said pinion gear includes a first engaging gear and a second engaging gear;
   said first engaging gear engaging a first stage gear rack to move said first stage relative to said second stage;
   said second engaging gear engaging a second stage gear rack to move said second stage relative to said fixed plate.

2. The system of claim 1 wherein said pinion gear operates to move said first stage and said second stage simultaneously.

3. The system of claim 1 wherein said first stage includes a tabletop for supporting a patient.

4. The system of claim 1 wherein said first stage includes first stage bearing rails for structurally supporting said first stage.

5. The system of claim 4 wherein said first stage bearing rails are positioned so as not to interfere with the imaging area of said imaging apparatus.

6. The system of claim 5 wherein said fixed plate includes second stage bearing rails for structurally supporting said second stage; wherein said first stage bearing rails are positioned directly over said second stage bearing rails.

7. The system of claim 1 wherein said fixed plate includes at least one stop block for arresting movement of said first stage.

8. The system of claim 1 wherein said first engaging gear has a first diameter and said second engaging gear has a second diameter.

9. The system of claim 8 wherein said first diameter differs from said second diameter.

10. The system of claim 8 wherein said first diameter is the same as said second diameter.

11. The system of claim 1 wherein said fixed plate includes second stage bearing rails for structurally supporting said second stage.

12. The system of claim 11 wherein said second stage bearing rails are positioned so as not to interfere with the imaging area of said imaging apparatus.

13. A method for positioning an imaging table in an imaging system, said imaging system including a first stage, a second stage, a fixed plate, and a pinion gear mounted in said second stage wherein said pinion gear includes a first engaging gear and a second engaging gear, said method including the steps of:

said first engaging gear engaging a first stage gear rack to move said first stage relative to said second stage;

said second engaging gear engaging a second stage gear rack to move said second stage relative to said fixed plate.

14. The method of claim 13 wherein said engaging step includes engaging a first stage gear rack included in said first stage with an operative surface of a pinion gear included in said second stage.

15. A system for positioning an imaging table in an imaging apparatus, said system including:

three or more stages; and a pinion gear operating to move said three or more stages relative to each other.

16. A system for positioning an imaging table in an imaging apparatus, said system including:

three or more stages; and a pinion gear operating to move at least three of said three or more stages relative to each other.

* * * * *